(12) United States Patent
Hu et al.

(10) Patent No.: US 9,075,070 B2
(45) Date of Patent: Jul. 7, 2015

(54) HTS FLUORESCENCE POLARIZATION ASSAY FOR INHIBITORS OF KEAP1-NRF2 INTERACTION

(75) Inventors: Longqin Hu, Belle Mead, NJ (US); Daigo Inoyama, Cherry Hill, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/369,902

(22) Filed: Feb. 9, 2012

(65) Prior Publication Data

US 2012/0202298 A1  Aug. 9, 2012

Related U.S. Application Data

(60) Provisional application No. 61/441,179, filed on Feb. 9, 2011.

(51) Int. Cl.
| | |
|---|---|
| *G01N 33/53* | (2006.01) |
| *G01N 33/68* | (2006.01) |
| *C07K 14/47* | (2006.01) |
| *G01N 21/64* | (2006.01) |

(52) U.S. Cl.
CPC ........ *G01N 33/6875* (2013.01); *C07K 14/4702* (2013.01); *G01N 21/6445* (2013.01); *G01N 2333/4703* (2013.01); *G01N 2500/02* (2013.01)

(58) Field of Classification Search
None
See application file for complete search history.

(56) References Cited

U.S. PATENT DOCUMENTS

2010/0029012 A1 *  2/2010  Kern et al. .................... 436/501

OTHER PUBLICATIONS

Wu, et al. Efficient amidation from carboxylic acids and azides via Selenocarboxylates: Application to the coupling of amino acids and peptides with azides. J. Org. Chem 2007, 72, 765-774.
Li, et al. Crystal Structure of the Kelch Domain of Human Keap1. J Biol Chem 2004, 279, 54750-54758.
Li, et al. Crystallization and initial crystallographic analysis of the Kelch domain from human Keap1. Acta Crystallographica Section D 2004, 60, 2346-2348.

* cited by examiner

*Primary Examiner* — Michael Pak
(74) *Attorney, Agent, or Firm* — Fox Rothschild LLP (57) ABSTRACT

Disclosed are methods and kits for identifying modulators of the Keap1-Nrf2-ARE pathway. In particular, a high throughput fluorescent polarization assay is described that identifies small molecules that inhibit the binding of a fluorescently labeled Nrf2 peptide with the kelch domain of the Keap1 protein. Also provided are probes that can be used in the described fluorescent polarization assay. The small molecules identified using the described assay are useful for combating oxidative stress-related disorders, such as those associated with cancer, emphysema, Huntington's disease, light-induced retinal damage, and stroke.

8 Claims, 4 Drawing Sheets

HTS FLUORESCENCE POLARIZATION ASSAY FOR INHIBITORS OF KEAP1-NRF2 INTERACTION

CROSS REFERENCE TO RELATED APPLICATION

This application claims the benefit of U.S. Provisional Application No. 61/441,179 filed Feb. 9, 2011, the disclosure of which is incorporated herein by reference in its entirety.

STATEMENT REGARDING FEDERALLY FUNDED RESEARCH

This invention was made with government support under Grants R03CA125868 and R01CA133791 awarded by the National Institutes of Health. Accordingly, the U.S. Government has certain rights in this invention.

BACKGROUND OF THE INVENTION

The processes of inflammation and oxidative stress are important in the pathogenesis of many diseases including cancer, Alzheimer's and Parkinson's diseases, asthma, atherosclerosis, diabetes, inflammatory bowel disease, multiple sclerosis, osteoarthritis and rheumatoid arthritis. Inflammation produces large amounts of reactive oxygen and nitrogen species that can induce oxidative damage to DNA and other cellular components; our bodies have evolved defensive mechanisms to protect our cells in addition to repair the DNA damage. Among the protective mechanisms are the various antioxidant scavengers and cytoprotective enzymes.

The expression of genes that encode these oxidative stress response enzymes are regulated through a cis-acting antioxidant response element (ARE) found in the promoter region of these genes. Nuclear factor E2-related factor 2 (Nrf2), a member of the Cap n'Collar (CNC) family of proteins, plays a major role in the oxidative stress response as the transcription factor that binds to the ARE to induce the coordinated expression of antioxidant and cytoprotective genes. It contains a highly conserved basic leucine zipper (bZIP) structure characteristic of the CNC transcription factors and requires a small Maf protein as a partner for nuclear transport and DNA binding. The interaction of Nrf2-Maf heterodimer with the cis-acting ARE is essential for the upregulation of oxidative stress response by Nrf2. Nrf2 is the central transcription factor that interacts with ARE to induce the expression of cytoprotective genes.

By comparing the amino acid sequences of Nrf2 across different species, 6 conserved homologous domains (Neh1 to Neh6 domains) of Nrf2 have been identified. Of these domains, the C-terminal Neh1 contains the bZIP domain for DNA binding with Maf, a nuclear transcription factor, and the N-terminal Neh2 domain acts as the regulatory domain by interacting with the cytoplasmic redox sensor protein, Keap1 (Kelch-like ECH-associated protein 1). Keap1 is a BTB-kelch protein consisting of five distinct domains: NTR (N-terminal region), BTB (broad complex, tramtrack, and brick a'brac), IVR (intervening region), DGR (double glycine repeat) or Kelch, and CTR (C-terminal region). The Kelch domain is a 6 bladed β-propeller in which each blade is comprised of four β-strands. Along with the CTR domain, the Kelch domain contributes to the complex formation with the N-terminal Neh2 domain of Nrf2. The BTB domain of Keap1 is a protein-protein interaction motif involved in the homodimer formation.

The N-terminal BTB domain of Keap1 interacts with Cul3, a member of the cullin family of E3 ubiquitin-protein ligases. Thus, Keap1 acts as the substrate adaptor protein that bridges the interaction between Cul3 and Nrf2 through its N-terminal BTB and the C-terminal Kelch domains. Normally, this Cul3-based E3 ubiquitin ligase complex functions to sequester Nrf2 in the cytoplasm by targeting multiple lysine residues in the Neh2 domain of Nrf2 for ubiquitination. The IVR domain of Keap1 contains a cysteine-rich region that acts as the primary sensor of oxidative response. Specifically, the modification of two highly reactive cysteine residues, C273 and C288, is believed to lead to the dissociation of Keap1-Nrf2 complex, the subsequent translocation of Nrf2 into the nucleus, and the ultimate activation of ARE genes. Disrupting the Keap1-Nrf2 complex may increase the body's defense against carcinogens and reactive oxygen species generated during oxidative stress by inducing the expression of ARE-regulated genes and upregulating the expression of oxidative stress response enzymes. Thus, the Keap1-Nrf2 complex in the ARE signaling pathway is believed to be the key target for cancer chemoprevention.

The DLG and the ETGE (SEQ ID NO:8) motifs within the Neh2 domain of Nrf2 are two evolutionary conserved motifs of CNC family of proteins. The DLG motif has been reported to be involved in ubiquitin-dependent degradation of Nrf2, while the ETGE motif has been reported to be essential for the Keap1 regulation of Nrf2 activity. Although both motifs bind to the same site in Keap1, the ETGE motif was reported to be approximately 100-fold higher in affinity to Keap1 than the DLG motif. Several different ETGE-containing peptides have been reported to displace Nrf2 from Keap1. The longer ETGE-containing 14mer and 16mer Nrf2 peptides (H-LQLDEETGEFLPIQ-OH (SEQ ID NO:10) and H-AFFAQLQLDEETGEFL-OH) (SEQ ID NO:7) were able to effectively displace the Nrf2 protein from the Keap1:Nrf2 complex; the binding affinity(K) between the longer Nrf2 peptides and the Keap Kelch domain was found to be as low as 20 nM as measured by isothermal titration calorimetry (ITC). The shorter 10mer Nrf2 peptide (H-LDEETGEFLP-OH) (SEQ ID NO:11) also displaces the Nrf2 protein from the complex, although it is much less effective than the longer Nrf2 peptides. With the exception of these Nrf2-derived peptides, there are currently no known small molecules that can directly interfere with the protein-protein interaction between Keap1 and Nrf2.

SUMMARY OF THE INVENTION

In one aspect, the present invention is directed in part to a method for identifying an agent that inhibits a Keap1-Nrf2 interaction, the method having the steps of: (1) providing a mixture including a Keap1-Kelch domain protein and a fluorescently labeled Nrf2 peptide that is capable of binding the Keap1-Kelch domain protein; (2) adding a test agent to the mixture; (3) determining the difference in the amount of fluorescently labeled Nrf2 peptide bound to the Keap1-Kelch domain protein in the presence and absence of the test agent; and (4) identifying the test agent as an inhibitor of the Keap1-Nrf2 interaction if the amount of fluorescently labeled Nrf2 peptide bound to the Keap1-Kelch domain protein in the presence of the test agent is less than in the absence of the test agent.

In certain embodiments, step (3) includes the steps of: (a) determining the fluorescence polarization value of the fluorescently labeled Nrf2 peptide in the solution; (b) determining the fraction of fluorescently labeled Nrf2 peptide bound to the Keap1-Kelch domain protein from the fluorescence polarization value; and (c) comparing the fraction of fluorescently labeled Nrf2 peptide bound to the Keap1-Kelch domain protein to the fraction of fluorescently labeled Nrf2 peptide bound to the Keap1-Kelch domain protein in the absence of the test compound. Step (b) may include converting the fluorescence polarization values to anisotropy values.

The above described method may also be used to determine an inhibition constant ($K_i$) value for the agent. This may be calculated by performing the steps (1)-(4) a plurality of times, each time with a different concentration of the agent.

In certain embodiments, the fluorescently labeled Nrf2 peptide used in the assay comprises an amino acid sequence selected from the group consisting of SEQ ID NO: 1, SEQ ID NO:2, SEQ ID NO:3, SEQ ID NO:4. SEQ ID NO:5, SEQ ID NO:6, and SEQ ID NO:7. Additionally, the N-terminus of the Nrf2 peptide may be capped with an acetyl group and/or the C-terminus of the Nrf2 peptide may be capped with an amide group.

The Nrf2 peptide may be labeled with a fluorophore, for example fluorescein isothiocyanate, BODIPY-FL, Cy3B, Cy5 and other fluorophores known to those of skill in the art. The peptide may be end labeled or labeled on a side chain by methods known in the art.

In another aspect, the present invention is directed to a kit for detection of an agent that inhibits a Keap1-Nrf2 interaction. The kit comprises individually packaged containers of a Keap1-Kelch domain protein and an Nrf2 peptide that is capable of binding the Keap1-Kelch domain protein. The kit may further comprise reagents for fluorescently labeling the Nrf2 peptide. The Nrf2 peptide may be fluorescently labeled. The kit may further include at least one reagent for performing a competitive binding assay to determine if the agent inhibits the Keap1-Nrf2 interaction. The kit may also include a device to measure the polarization of the fluorescently labeled Nrf2 peptide.

In yet another aspect, the present invention is directed in part to a probe for performing a fluorescent polarization assay comprising an Nrf2 peptide labeled with a fluorophore, wherein the Nrf2 peptide comprises an amino acid sequence selected from the group consisting of SEQ ID NOs 1-7. In a preferred embodiment, the Nrf2 peptide comprises the amino acid sequence of SEQ ID NO 2. The probe may be fluorescently labeled, for example with fluorescein isothiocyanate. Additionally, in certain embodiments, the C-terminus of the Nrf2 peptide is capped with an amide group.

The methods, kits and probes of the invention are useful to be used to screen in high throughput screening (HTS) format for small molecules that interfere with Keap1-Nrf2 interaction and act as activators of Nrf2.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention.

The present invention provides a method to identify small molecules that disrupt the interaction of Nrf2 transcription factor with the Kelch domain of the Keap1 protein to form an Nrf2-Keap1 complex. The method provides a high throughput solution-based fluorescence polarization (FP) assay using a fluorescently labeled Nrf2 peptide as a probe and the Keap1 Kelch domain as a protein target. This FP assay enables the discovery and development of novel small molecules as direct inhibitors of Keap1-Nrf2 interaction at the protein-protein interface.

These inhibitors mimic the actions of reactive oxygen species and electrophiles like isothiocyanates and Michael acceptors in the induction of cytoprotective enzymes but are more selective and specific against the Keap-Nrf2 interaction. Inhibitors identified by the provided assay are useful for combating oxidative stress-related disorders associated with cancers, emphysema, Huntington's disease, light-induced retinal damage, cardiovascular disease, Parkinson's disease, Alzheimer's disease, and stroke.

The Nrf2 peptide probes used for the present assay are based on the ETGE (SEQ ID NO:8) motif at the highly conserved Keap1 binding region within the Neh2 domain of Nrf2 protein. The probe may be selected from Nrf2 peptides of different lengths, ranging from 8mers to 16mers, and comprising the amino acid sequence ETGE (SEQ ID NO:8). In a preferred embodiment, the peptide has an amino acid sequence selected from the group consisting of DEETGEFL (SEQ ID NO:1); LDEETGEFL (SEQ ID NO:2); QLDEETGEFL (SEQ ID NO:3); LQLDEETGEFL (SEQ ID NO:4); QLQLDEETGEFL (SEQ ID NO:5); FAQLQLDEETGEFL (SEQ ID NO:6); and AFFAQLQLDEETGEFL (SEQ ID NO:7).

Prior to use in the assay, the Nrf2 peptide is fluorescently labeled with a fluorophore. While fluorescein isothiocyanate (FITC) is the preferred fluorophore, other embodiments of this invention may utilize other labeling fluorophores, for example BODIPY-FL, Cy3B, and Cy5. The fluorescent labeling of the Nrf2 peptides at the N-terminus does not significantly affect the binding properties of the probes as the unlabeled peptides exhibit a similar trend in the binding to the Keap1 Kelch domain as the FITC-labeled peptides.

To increase the binding affinity of the Nrf2 peptide probe to Keap1 Kelch domain, in certain embodiments, the C-terminus of the probe is capped with an amide group. Similarly, in other embodiments, the N-terminus may be capped with an acetyl group if fluorescent labeling is done on the side chain.

End capping is a common technique used in peptide chemistry to obtain peptides that better resemble proteins by removing the otherwise ionizable end groups of the peptide segments. For example, the N-acetylation of 9mer Nrf2 peptide (SEQ ID NO:2) by acetic anhydride yields a short Nrf2 peptide (SEQ ID NO:13) capable of inhibiting the interaction between Keap1 Kelch domain and Nrf2 at an $IC_{50}$ similar to the 12mer (SEQ ID NO:5) and the 14mer (SEQ ID NO:6) Nrf2 peptides.

In one embodiment, the present invention provides a FITC-9mer Nrf2 amide (FITC-LDEETGEFL-$NH_2$) (SEQ ID NO:12) that is useful as a preferred peptide probe to carry out the FP assay of the present invention. The FITC-9mer Nrf2 amide probe has a low $K_d$ and a high dynamic range. Compared with FITC-9mer Nrf2 acid (SEQ ID NO:2), C-terminal amidation offered a greater than 2-fold increase in the binding affinity as well as a significant increase in dynamic range. The increase in dynamic range for FITC-9mer Nrf2 amide over the FITC-16mer Nrf2 peptide represents a significant decrease in the "propeller effect" seen in FITC-16mer Nrf2 peptide. The "propeller effect" is caused by flexibility of the fluorescent dye on a tracer, which depolarizes the fluorescence signal of the bound complex. Applicants' approach of shortening the peptide probe length enabled the attachment of the fluorescent dye closer to the peptide binding site to increase the tracer rigidity without adversely affecting the peptide's binding affinity. This is consistent with the X-ray crystal structure study of 16mer Nrf2 peptide-Keap1 Kelch domain complex, which showed that the 16mer Nrf2 peptide is much longer than the length of ETGE motif needed to bind Keap1 and several of the N-terminal residues were exposed to solvent and structurally undefined in the complex. Thus, Applicants successfully optimized the fluorescent Nrf2 peptide probe for increased affinity and dynamic range. However, it should be understood that any of the other probes described herein are suitable for carrying out the presently described FP assay.

The Keap1-Kelch domain is preferably a human Keap1-Kelch domain and may be produced recombinantly or by methods known in the art. The Keap1-Kelch domain may have the amino acid sequence GSSHHHHHSSGLVPRG-SHLAPKVGRLIYTAGGYFRQSL-SYLEAYNPSDGTWLRLADLQ VPRSGLAGCVVG-GLLYAVGGRNNSPDGNTDSSALDCYNPMTNQ WSPCAPMSVPRNRI GVGVIDGHIYAVGGSHGCI-HHNSVERYEPERDEWHLVAPMLTRRI-GVGVAVLNRLLYA VGGFDGTNRLNSAECYYPERNE-WRMITAMNTIRSGAGVCVLHNCIYAAGGYDGQDQL NSVERYDVETETWTFVAPMKHRRSAL-GITVHQGRIYVLGGYDGHTFLDSVECYDPDTD TWSEVTRMTSGRSGVGVAVT (SEQ ID NO:15). Conservatively modified variants of the amino acid sequence of SEQ ID NO:15. are also included. One of skill will recognize that individual substitutions, deletions or additions to a nucleic peptide, polypeptide, or protein sequence which alter, add or delete a single amino acid or a small percentage of amino acids in the encoded sequence are "conservatively modified variants", including where the alteration results in the substitution of an amino acid with a chemically similar amino acid. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

In a competition FP binding assay of the present invention, a mixture including a Keap1-Kelch domain protein and a fluorescently labeled Nrf2 peptide that is capable of binding the Keap1-Kelch domain protein is first provided. The small molecule to be tested is then added to the mixture. The difference in the amount of fluorescently labeled Nrf2 peptide bound to the Keap1-Kelch domain protein in the presence and absence of the test agent is then determined. The small molecule is identified as an inhibitor of the Keap1-Nrf2 interaction if the amount of fluorescently labeled Nrf2 peptide bound to the Keap1-Kelch domain protein in the presence of the test agent is less than in the absence of the test agent. By comparing the change in the amount of fluorescently labeled Nrf2 peptide bound to the Keap1-Kelch domain protein in the presence of a variety of test agents that undergo the assay individually, one can determine a relative potency of the identified inhibitors.

FP may be measured by methods known in the art, for example by using a fluorescence spectrometer or a well-plate based fluorescence detector, using excitation and emission filters appropriate for a particular fluorophore.

In one embodiment, the assay is adapted for high throughput screening, for example by using multiwall plates, for example 96-well or 384-well plates, preferably having black nonbinding surfaces. A liquid handling robot may be used to deliver solutions to the wells.

One of skill in the art can determine suitable reaction conditions for performing the assays of the present invention. In one preferred embodiment, a concentration of about 20 nM to 50 nM, and more preferably about 40 nM, of the fluorescently labeled Nrf2 peptide is used. In another embodiment, a concentration of about 200 nM to 600 nM, and more preferably about 400 nM, of the Keap1-Kelch domain protein is used. In another preferred embodiment, the test agent is used at an initial concentration of from 10 µM to about 100 µM, and serially diluted down to 0.5 nM or 5 nM. In another preferred embodiment, the mixture of the Keap1-Kelch domain protein, fluorescently labeled NRF2 peptide, and test agent is allowed to equilibrate at room temperature before FP measurements, for example for about 30 minutes.

Using the competition FP binding assay, Applicants determined that a 16mer-Nrf2 peptide (SEQ ID NO:7) has a strong inhibitory activity with an $IC_{50}$ of 101 nM, thus a high binding affinity for the Keap1 Kelch domain. The inhibitory activity decreases with decreasing peptide length; the minimum number of residues required for binding to Keap1 Kelch domain is 8 as indicated by the complete loss of any binding affinity in a 7mer Nrf2 peptide (EETGEFL, SEQ ID NO:9) and retention of some inhibitory activity in an 8mer Nrf2 peptide (SEQ ID NO:1).

Applicants confirmed the utility of the FP assay for HTS applications by using the FP assay at 10 nM FITC-labeled 9mer Nrf2 amide (SEQ ID NO:12) and 100 nM Keap1 Kelch domain protein to screen about 1800 compounds in duplicates at 100 µM in 384-well plates. The compounds came from two libraries; the NCI diversity set II of 1360 and the NIH Clinical Collection of 450. In all of the screening, included were three sets of controls in each plate including probe only, probe plus Keap1 Kelch domain protein, and probe plus Keap1 Kelch domain protein in the presence of 1 μM N-Ac-9mer Nrf2 peptide. The N-Ac-9mer Nrf2 peptide (SEQ ID NO:13) is a known inhibitor of the Keap1-Nrf2 interaction with an $IC_{50}$ of about 200 nM and at 1 μM, it produces about 80% inhibition and serves as the positive control. The robustness and reproducibility of the assay is indicated by the Z'-factor calculated for each plate using anisotropy data for wells containing probe plus Keap1 Kelch domain protein in the presence and absence of 1 μM N-Ac-9mer Nrf2 peptide inhibitor. Z' is greater than 0.5 for all 26 plates that were screened with an average Z' of 0.596 and a standard deviation of 0.045. The compounds with the highest Z-scores (>3) are considered the initial hits as potential inhibitors of Keap1-Nrf2 interaction.

The present invention may also comprise a kit for detection of an agent that inhibits the Keap1-Nrf2 interaction. The kit may comprise individually packaged containers of a Keap1-Kelch domain protein and an Nrf2 peptide that is capable of binding the Keap1-Kelch domain protein. The kit may further comprise reagents for fluorescently labeling the Nrf2 peptide. The Nrf2 peptide may be fluorescently labeled. This kit may further include at least one reagent for performing a competitive binding assay. The kit will allow for one to carry out the methods of the present invention to identify small molecules that act as inhibitors of the Keap1-Nrf2 interaction. In certain embodiments, the kit will also allow one to determine the potency of the small molecule that is identified as an inhibitor of the Keap 1-Nrf2 interaction.

The following provides the materials and methods used to carry out one embodiment of the present invention. It should not be used to limit the scope of the invention.

Examples

Materials

Fmoc-protected amino acids, N,N,N-diisopropylethylamine (DIPEA, Hunig's base), N,N,N-triethylamine (TEA), 1-hydroxybenzotriazole (HOBt). N-methylpyrrolidin-2-one (NMP), O-(benzotriazol-1-yl)-N,N,N',N'-tetramethyluronium hexafluorophosphate (HBTU), (benzotriazol-1-yloxy)tripyrrolidinophosphonium hexafluorophosphate (PyBOP), Wang resin, 2-chlorotrityl chloride (2CTC) resin, and Rink-amide resin are available from Chem-Impex (Wood Dale, Ill.). N,N'-Diisopropylcarbodiimide (DIC) and 4-dimethylaminopyridine (DMAP) are available from Acros (Morris Plains, N.J.). Fluorescein-5-isothiocyanate (FITC) and boron-dipyrromethene (BODIPY) FL $C_5$-NHS are available from Molecular Probes (Carlsbad, Calif.). The cyanine dyes such as Cy3B NHS and Cy5 NHS are available from GE Healthcare (Piscataway, N.J.). All other reagents and solvents used are available from Sigma-Aldrich (St. Louis, Mo.).

Peptide Synthesis

All peptides were synthesized using solid-phase techniques on a Model 90 automated peptide synthesizer from Advanced ChemTech (now AAPPTec, Louisville, Ky.). Standard Fmoc chemistry was utilized for the synthesis of Nrf2 peptides with amino acid side chains protected by either Boc or tert-butyl esters where necessary. The series of Nrf2 peptides were synthesized on either Wang or 2-chlorotrityl chloride (2CTC) resin, while the Nrf2 peptide amides were synthesized on Rink Amide resin. For the attachment of first amino acid to Wang resin, a solution of N-Fmoc-amino acid (3 eq. relative to resin substitution), DIC (3 eq.), DMAP (0.1 eq.), and DIPEA (4 eq.) in 10% NMP/DCM was transferred to a reaction vessel containing the pre-swollen resin. The reaction was shaken overnight under $N_2$ and the unreacted hydroxyl groups on the Wang resin were capped with acetic anhydride (2 eq. relative to resin substitution) in presence of pyridine (2 eq. relative to resin substitution).

For the attachment of first amino acid to Rink-amide resin, the resin was first deprotected using 20% piperidine/NMP solution for 30 minutes and Fmoc-amino acid was loaded onto the resin using HBTU/HOBt coupling method. The attachment of the first amino acid was confirmed by negative ninhydrin test.

For the attachment of first amino acid to 2CTC resin, a solution of Fmoc-amino acid (1 eq. relative to resin substitution) and DIPEA (1.2 eq. relative to amino acid) in NMP was added to the pre-swollen resin. The reaction was shaken for 3 h at room temperature under $N_2$ and the residual chloride groups on the 2CTC resin were deactivated by MeOH in the presence of pyridine (1 eq. relative to resin substitution) for 30 minutes.

The Fmoc protecting group was removed with 20% piperidine in NMP for 30 min at room temperature and the subsequent Fmoc-protected amino acids (3 eq. relative to resin loading) were coupled to the deprotected resin through HOBt-activated esters. The reaction was stirred with $N_2$ bubbling for 3 h at room temperature and the completion of the coupling reactions were confirmed by the ninhydrin test. After successful coupling of all amino acids, the assembled peptides were cleaved from the resin with a trifluoroacetic acid (TFA) solution containing 2.5% triisopropylsilane (TIS) and 2.5% water. The acid-sensitive side chain protecting groups were removed simultaneously during the cleavage step. The crude peptide was obtained by concentrating the TFA solution with $N_2$ followed by precipitation with dropwise addition of diethyl ether at 0° C. The precipitate was collected by centrifugation and washed 3 times with fresh ice-cold diethyl ether.

Nrf2 peptides of different length (8mer to 16mer) were synthesized using the above procedure. Amino acid sequences of these peptides were based on the ETGE motif at the highly conserved Keap1 binding region within the Neh2 domain of Nrf2 protein. The ETGE motif is known to bind to Keap1 with 100-fold higher affinity than the DLG motif, thus indicating that fluorescently labeled peptides based on the ETGE motif could be used as the probe with high binding affinity to Keap1 Kelch domain. The length of the Nrf2 peptides also affects Keap1 binding with the ETGE-containing 16mer Nrf2 peptide (H-AFFAQLQLDEETGEFL-OH) (SEQ ID NO:7) reported to have a dissociation constant ($K_d$) of approximately 20 nM, while the shorter 10mer Nrf2 peptide (H-LDEETGEFLP-OH) (SEQ ID NO:11) was reported to have weaker binding affinity.

The Nrf2 peptides synthesized were cleaved from the resin prior to FITC labeling in order to avoid the Edman degradation of the FITC-labeled Nrf2 peptides during TFA cleavage of the peptides from the resin. The purity of the crude peptides upon cleavage from the resin was sufficient for direct N-terminal labeling without further purification. The lack of solubility of the longer peptides in aqueous medium required the use of neutral buffer (10 mM ammonium acetate/acetonitrile, pH 7.6) as the mobile phase for the purification of the 14mer and the 16mer Nrf2 peptides. Although the cleaved peptides have an ionizable N-terminal amino group, the solubility of the longer peptides was lower in acidic mobile phase (0.1% trifluoroacetic acid, pH 2). The decrease in the solubility of the longer peptides in aqueous medium is attributed to the increased propensity for aggregation with the addition of β-sheet forming hydrophobic residues and the formation of intermolecular hydrogen bonds between the peptide backbones.

Reversed-Phase HPLC Purification

All peptides were purified on a Gilson preparative HPLC system using a reversed-phase BDS-Hypersil $C_{18}$ column (150×20 mm). In general, the crude peptide sample obtained after cleavage from the resin was re-dissolved in 50% acetonitrile in water for injection into the HPLC system. An acetonitrile gradient containing 0.1% TFA was used to elute the peptides from the column with the exception of 16mer Nrf2 peptide (H-AFFAQLQLDEETGEFL-OH) (SEQ ID NO:7), which lacked sufficient solubility under the acidic conditions. For this peptide, an acetonitrile gradient containing 10 mM ammonium acetate pH 7.6 was used to elute the product from the column. The peptides were obtained at >95% purity and their identities confirmed by LC-MS and high-resolution mass spectrometry.

Peptide Modification and Labeling

Fluorescein-labeled peptides were prepared by modification of purified peptides with FITC according to the manufacturer's standard protocol. The peptide (1 mg) was dissolved in 0.5 mL of 100 mM sodium carbonate buffer at pH 8.5 and FITC (2 eq.) was added to the solution. The reaction was stirred at room temperature for 12 h while protected from light. The progress of the labeling reaction was monitored by the disappearance of the starting peptide using LC-MS. A 1 N solution of sodium bisulfate ($NaHSO_4$) was added to reduce the pH of the reaction to 2 and the precipitated crude modified peptide was collected by centrifugation. The product was purified by reversed-phase HPLC as described above. For labeling of the 9mer Nrf2 peptide amide (H-LDEETGEFL-$NH_2$) (SEQ ID NO: 2) with N-hydroxy succinimide (NHS) esters of BODIPY-FL, Cy3B and Cy5, the peptide was first dissolved in anhydrous DMSO containing 5 eq. of TEA, which was then followed by the addition of the NHS ester (1.2 eq.) in one portion. The reaction mixture was stirred for 12 h at room temperature protected from light. The reaction was acidified with formic acid before the mixture was diluted with water for reversed-phase HPLC purification.

The N-biotinyl 16mer Nrf2 peptide for the SPR binding assay (described below) was prepared on solid phase by reacting 2CTC resin-bound 16mer Nrf2 peptide (20.0 mg) with a 1 mL solution of biotin (12.4 mg, 5 eq.) pre-activated with HBTU (19.3 mg, 5 eq.) in NMP containing DIPEA (10.7 μL, 6 eq.). The biotinylated 16mer Nrf2 peptide was cleaved from the resin by a 3-h treatment of the resin-bound peptide with 95% TFA containing 2.5% TIS and 2.5% $H_2O$. The crude peptide obtained after ether precipitation was re-dissolved in 50% acetonitrile in 10 mM $NH_4OAc$ and purified on a reversed-phase HPLC using the same conditions as in the purification of the free 16mer Nrf2 peptide as described earlier.

The N-acetylation of the 9mer Nrf2 peptide and 9mer Nrf2 peptide amide was performed on the resin-bound 9mer Nrf2 peptides. Briefly, the resin was pre-swollen in DCM for 30 min and washed 3 times with NMP. The resin was treated with acetic anhydride (5 eq.) and pyridine (5 eq.) in NMP for 30 min and the capping reaction was monitored by ninhydrin test. The crude peptide was cleaved from the resin with trifluoroacetic acid (TFA) containing 2.5% triisopropylsilane (TIS) and 2.5% water as the scavengers. The peptide was purified on a reversed-phase HPLC using the conditions described earlier.

To test the effect of C-terminal end capping of the FITC-labeled Nrf2 peptides, the FITC-8mer and FITC-9mer Nrf2 peptide amide were synthesized using the Rink amide resin. As shown in Table 1 and FIG. 2, the effect of N-terminal FITC-labeling is similar to the effect of N-acetylation of 9mer Nrf2 peptide and the FITC-labeled Nrf2 peptides longer than 8 amino acids in length differ slightly in terms of their binding affinity to Keap1 Kelch domain. In addition, the C-terminal end-capping of FITC-9mer Nrf2 peptide as the amide increased the binding affinity of the probe by 2-fold as compared to the FITC-9mer Nrf2 peptide. However, similar increase in binding affinity to Keap1 was not observed between the FITC-8mer Nrf2 peptide and the FITC-8mer Nrf2 amide.

TABLE 1

The binding affinity and dynamic range for FITC-labeled Nrf2 peptides.[a]

| Peptide | | $K_d$ (nM) | Dynamic Range (ΔmA) |
|---|---|---|---|
| FITC-8mer Nrf2 | FITC-DEETGEFL-OH | ~750[b] | —[c] |
| FITC-8mer Nrf2-$NH_2$ | FITC-DEETGEFL-$NH_2$ | ~1000[b] | —[c] |
| FITC-9mer Nrf2 | FITC-LDEETGEFL-OH | 65.1 ± 9.7 | 97.3 |
| FITC-9mer Nrf2-$NH_2$ | FITC-LDEETGEFL-$NH_2$ | 25.6 ± 10.8 | 109.8 |
| FITC-10mer Nrf2 | FITC-QLDEETGEFL-OH | 30.1 ± 6.1 | 73.5 |
| FITC-11mer Nrf2 | FITC-LQLDEETGEFL-OH | 47.7 ± 7.4 | 96.3 |
| FITC-12mer Nrf2 | FITC-QLQLDEETGEFL-OH | 44.5 ± 12.9 | 70.6 |
| FITC-14mer Nrf2 | FITC-FAQLQLDEETGEFL-OH | 61.9 ± 6.5 | 64.2 |
| FITC-16mer Nrf2 | FITC-AFFAQLQLDEETGEFL-OH | 28.7 ± 5.7 | 80.1 |

[a]Anisotropy measurements for the FP binding assay were performed as described under methods section. $K_d$ values were determined using equation 5 and the dynamic range was calculated as the difference in the free and the bound anisotropy of the respective ligand.
[b]The binding affinity of the FITC-labeled 8mer Nrf2 peptides were estimated using the anisotropy of the fully bound FITC-9mer Nrf2 peptide.
[c]The higher end of the dynamic range could not be determined due to low binding affinity.

As shown in Table 1, the dynamic range of the FITC-9mer Nrf2 peptide amide (FITC-LDEETGEFL-NH$_2$) (SEQ ID NO:2) was the highest among FITC-labeled Nrf2 peptides tested with 109.8 mA increase in anisotropy upon binding to Keap1 Kelch domain. The FITC-14-mer Nrf2 peptide (FITC-FAQLQLDEETGEFL-OH) (SEQ ID NO:6) was shown to have the smallest dynamic range of 64.2 mA increase in anisotropy upon binding with a K$_d$ of 61.9 nM and the FITC-16-mer Nrf2 peptide (FITC-AFFAQLQLDEETGEFL-OH) (SEQ ID NO:7) based on the reported sequence exhibited a mediocre dynamic range of ΔmA=80.1 mA, but a good binding affinity with a K$_d$ of 28.7 nM.

Peptide Concentration Determination

The concentrations of unlabeled Nrf2 peptide solutions were determined by amino acid analysis through acid hydrolysis and o-phthaldialdehyde (OPA)/N-Boc-L-cysteine (NBC) derivatization as described by Wu, X.; Hu, L. Efficient amidation from carboxylic acids and azides via Selenocarboxylates: Application to the coupling of amino acids and peptides with azides. *J. Org. Chem* 2007, 72, 765-774. 10 μL of peptide solutions were dried using a Savant Speedvac for 2 h at 45° C. and hydrolyzed by 6 N constant boiling HCl in a sealed hydrolysis vial under vacuum at 110° C. for 24 h with Cbz-L-phenylalanine as the control and L-tyrosine as the internal standard. After the hydrolysis reaction, the sample tubes were dried for 2 h at 45° C. using a Savant Speedvac prior to derivatization. The OPA/NBC derivatization solutions were prepared fresh by dissolving 11 mg of o-phthaldialdehyde (OPA) and 20 mg of N-Boc-L-cysteine (NBC) each in 1 mL of methanol. For derivatization, 10 μL of 1.0 mM L-tyrosine, 50 μL of 0.1 M Na$_2$B$_2$O$_7$ (pH 9.6), 50 μL deionized water, 20 μL OPA solution, and 20 μL NBC solution were added to each test tube containing the hydrolyzed peptide sample. The mixture was vortexed for 5 min at room temperature, then immediately analyzed by HPLC on a reversed-phase C$_1$a column (Waters Symmetry, 150×4.6 mm, 4 μm) using methanol and 10 mM phosphate buffer, pH 7.0 as the mobile phases at a flow rate of 0.5 mL/min. The elution started with an isocratic step of 30% methanol for 5 min, followed by a gradient from 30 to 60% methanol in 25 min. The concentration of the peptide was determined by calculating the ratio of the peak areas (λ=340 nm) of the OPA/NBC derivatized phenylalanine and the internal standard, L-tyrosine.

The concentrations of fluorescently labeled Nrf2 peptides were determined based on the absorbance of the fluorophores at their characteristic $λ_{max}$. Each of the fluorescently labeled Nrf2 peptides was dissolved in 10 mM HEPES buffer to give an estimated concentration of 1.0 mM. For fluorescein-labeled peptides, the UV absorbance of a diluted sample (50-100× dilution) was measured in triplicate at $λ_{max}$=494 nm (ε=68,000 M$^{-1}$cm$^{-1}$). For BODIPY, Cy3B, and Cy5-labeled Nrf2 peptides, the UV absorbances were measured at 504 nm, 563 nm, and 646 nm, respectively; the concentrations were calculated using molar extinction coefficients of 87,000 M$^{-1}$cm$^{-1}$, 130,000 M$^{-1}$cm$^{-1}$, and 250,000 M$^{-1}$cm$^{-1}$, respectively. These diluted samples were used as stock solutions for the fluorescence polarization assays.

Protein Expression and Purification of Human Keap1 Kelch Homain

The recombinant human Keap1 Kelch domain was expressed and purified as previously described by Li, X.; Zhang, D.; Hannink, M.; Beamer, L. J. Crystal Structure of the Kelch Domain of Human Keap1. *J Biol Chem* 2004, 279, 54750-54758; and Li, X.; Zhang, D.; Hannink, M.; Beamer, L. J. Crystallization and initial crystallographic analysis of the Kelch domain from human Keap1. *Acta Crystallographica Section D* 2004, 60, 2346-2348.

Anisotropy Measurements

All Fβ-assays were performed on a Wallac Victor 3V multilabel counter/plate reader (Perkin Elmer, Shelton, Conn.) using the excitation and emission filters appropriate for each fluorophore used in the binding experiment. The plates used for the FP measurements were the black NBS (nonbinding surface) Corning 3650 96-well or Corning 3575 384-well plates, loaded with 80 or 40 μL of assay solution per well. For fluorescein and BODIPY, 485 nm excitation and 535 nm emission filters were used. For Cy3B, excitation and emission filters of 560 nm and 650 m were used, respectively. For Cy5, 579 nm excitation and 670 nm emission filters were used. The buffer used for the FP assays was 10 mM HEPES pH 7.4 buffer containing 50 mM EDTA, 150 mM NaCl, and 0.005% Tween-20. All aqueous solutions were prepared using deionized water collected from a Millipore water purification system.

Fluorescence polarization was determined by measuring the parallel and perpendicular fluorescence intensity (F$_∥$ and F$_⊥$) with respect to the linearly polarized excitation light. The fluorescence polarization (P) and the anisotropy (A) are expressed by equations (1) and (2), respectively, and the anisotropy A is related to the P value by equation (3).

$$P = \frac{F_∥ - F_⊥}{F_∥ - F_⊥} \quad (1)$$

$$A = \frac{F_∥ - F_⊥}{F_∥ - 2F_⊥} \quad (2)$$

$$A = \frac{2P}{3 - P} \quad (3)$$

Applicants used anisotropy in the quantitative analysis because anisotropy values can be combined additively. In addition, total fluorescence (F$_∥$+2F$_⊥$) was calculated for each well to ensure that the fluorescence intensity was consistent with the amount of fluorescent probes used across all assay wells.

Measurement of Binding of Fluorescent Peptide Probes to Keap1 Kelch Domain

The binding of the fluorescently labeled Nrf2 peptides to Keap1 Kelch domain were determined by dose titration of the fluorescent peptide probes with varying concentrations of Keap1 Kelch domain protein. The maximum anisotropy achieved at a high concentration of Keap1 Kelch domain protein defines the upper end of the dynamic range for the peptide probe and the total fluorescence (F$_∥$+2F$_⊥$) at the high concentration of Keap1 Kelch domain protein can be used to calculate the Q-value, the quantum yield ratio of the bound and the free fluorescent peptide probe. Equation (4) is used to calculate $f_b$, the fraction of the bound probe, at a given concentration of Keap1 Kelch domain protein:

$$f_b = \frac{A_{obs} - A_{free}}{(A_{bound} - A_{obs})Q + (A_{obs} - A_{free})} \quad (4)$$

where $A_{obs}$, $A_{bound}$, $A_{free}$ refer to the observed anisotropy the at the given concentration of Keap1 Kelch domain protein, the anisotropy of probe when it is bound to Keap1 Kelch domain protein, and the anisotropy of the free probe, respectively. The $f_b$ data obtained can be fitted to the quadratic equation (5) to derive K$_d$ using SigmaPlot (SPSS, USA):

$$f_b = \frac{K_d + L_t + R_t - \sqrt{(K_d + L_t + R_t)^2 - 4L_tR_t}}{2L_t} \quad (5)$$

where $L_t$ is the concentration of total peptide probe used, which was fixed at 10 nM, and $R_t$ is the concentration of Keap Kelch domain protein, which varied between 0 and 2 µM.

Optimization of Fluorescently Labeled Nrf2 Peptide Probes

The X-ray crystal structure of 16mer Nrf2 peptide-Keap1 Kelch domain complex has shown that the 16mer Nrf2 peptide is much longer than the DxETGE motif. Several of N-terminal residues were exposed to solvent and structurally undefined in the complex. Therefore, the shorter DxETGE-containing Nrf2 peptides could retain the strong binding affinity to Keap1 Kelch domain and provide a higher dynamic range for the FP assay. In the optimization of the fluorescent Nrf2 peptide probe, Applicants successively deleted the N-terminal residues in the 16mer Nrf2 peptide and compared the Keap1 Kelch domain binding affinity and the FP dynamic range for the resulting shortened Nrf2 peptide probes.

Figure 1:
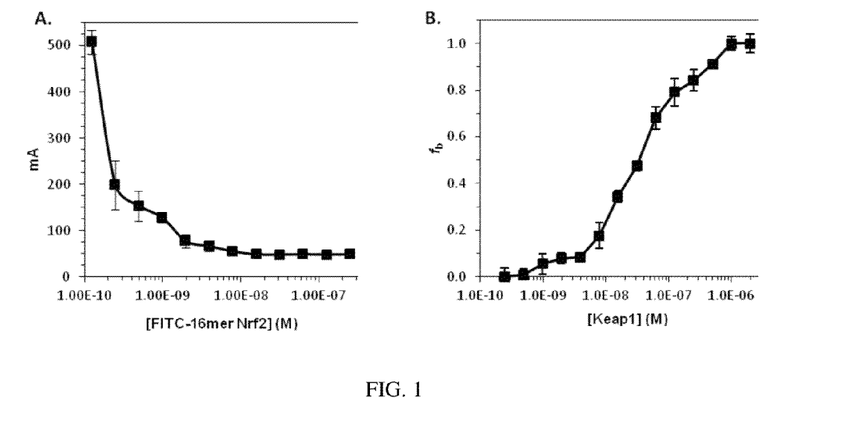
FIG. 1(A) shows the anisotropy of FITC-labeled 16mer Nrf2 peptide as a function of peptide probe concentration and FIG. 1(B) shows the plot of fraction bound of FITC-16mer Nrf2 peptide to Keap1 Kelch domain against Keap1 concentration.

Based on the FP binding assay shown in FIG. 1B, the FITC-labeled 16mer Nrf2 peptide has a $K_d$ of 28.7 nM. This level of affinity is in good agreement with the $K_d$ obtained using isothermal calorimetry (ITC). Although the FITC-labeled 16mer Nrf2 peptide has good binding affinity, the dynamic range of the 16mer peptide (ΔmA=80.1 mA) was relatively small. Applicants decided to shorten the sequence to obtain peptide probes with similar binding affinity but with a larger dynamic range. In principle, the ideal peptide probe for the FP assay is relatively short in length to avoid the "propeller effect" caused by the flexibility of the fluorescent dye on a tracer, which depolarizes the fluorescence signal of the bound complex.

Therefore, it is preferable to attach the fluorescent dye as close as possible to the peptide binding site to increase the tracer rigidity without adversely affecting the peptide's binding affinity.

Figure 2:
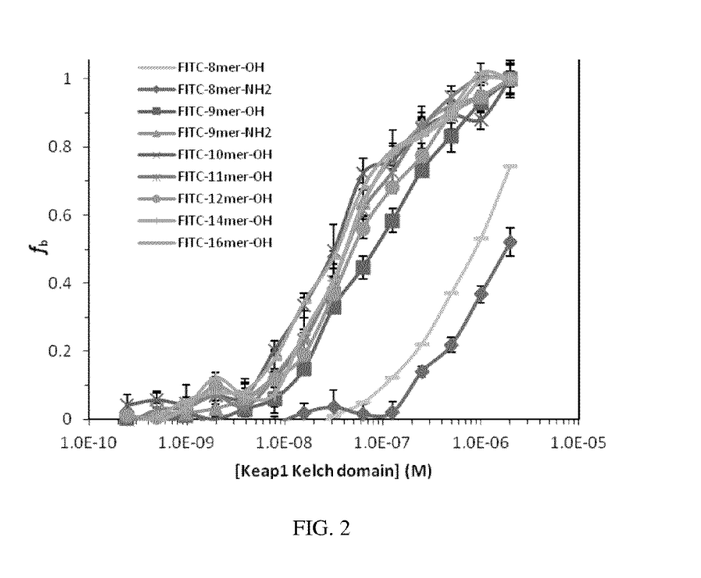
FIG. 2 displays the fraction bound plot of various FITC-labeled Nrf2 peptides to Keap1 Kelch domain against the Keap1 Kelch domain concentration.

As shown in Table 1 and FIG. 2, the binding of the FITC-labeled 8mer Nrf2 peptide (FITC-DEETGEFL-OH) (SEQ ID NO: 1) to Keap1 Kelch domain was too weak for regression analysis (est. $K_d$~0.75 µM). The binding of the FITC-labeled 9mer Nrf2 peptide (FITC-LDEETGEFL-OH) (SEQ ID NO: 2) to Keap1 Kelch domain was much stronger ($K_d$=65.1 nM) than the FITC-labeled 8mer Nrf2 peptide, although both peptides contain the necessary DxETGE motif. This indicates that the fluorescent dye is too close to the binding site in the case of the FITC-8mer Nrf2 peptide and adversely affected the binding of the peptide to the Keap1 Kelch domain and the 8mer Nrf2 peptide was not sufficient for binding to Keap1 Kelch domain. The binding affinity of the FITC-16mer Nrf2 peptide was the highest with a $K_d$ of 28.7 nM, which was approximately 2-fold higher in affinity to Keap1 Kelch domain as compared to the shorter FITC-9mer Nrf2 peptide. The equilibrium dissociation constants for the longer FITC-labeled Nrf2 peptides (11mer-14mer) were very close to that of the FITC-9mer Nrf2 peptide indicating that most of the bonding interactions between the Keap1 Kelch domain and Nrf2 reside in the 9mer Nrf2 peptide (LDEETGEFL) (SEQ ID NO: 2) and the binding affinity is not significantly affected by the peptide length as long as peptide contains the 9 amino acids in the DxETGE motif.

The relatively high dynamic range of the FITC-11mer Nrf2 peptide (ΔmA=96.3 mA) as compared to some of the shorter peptides was unexpected because of the additional amino acids outside of the DxETGE sequence. The dynamic range for the longer peptides was expected to be lower since the longer peptides contain several residues that extend out of the binding site of the DxETGE motif of Nrf2 and exposed to solvent. Therefore, the expected decrease in dynamic ranges of the assay for the longer peptides would have been due to the propeller effect, where the fluorophore extends out of the binding pocket and the flexibility of the fluorophore depolarizes the bound probe. The data shown in Table 1 does indicate an overall trend that the dynamic range decreases with increasing length of the peptide. This indicated that FITC-9mer Nrf2 peptide amide has the strongest binding affinity to Keap1 Kelch domain with a $K_d$ of 25.6 nM and the highest dynamic range of all FITC-labeled Nrf2 peptides synthesized with a ΔmA of 109.8 mA (288.5% increase in anisotropy upon binding). Thus, Applicants selected the FITC-9mer Nrf2 peptide amide as the fluorescent peptide probe for the FP assays.

Selection of the FP Assay Conditions

To determine the optimal conditions for the presently described FP assay, Applicants used the FITC-labeled 16mer Nrf2 peptide as the initial fluorescent probe to explore different assay conditions. Applicants measured the anisotropy of the fluorescently labeled 16mer Nrf2 peptide as a function of its concentration to select the optimal concentration of the probe for use in the FP binding assays. Anisotropy is a size-dependent, not concentration-dependent, property and the observed anisotropy in the presence of protein is related to the amount of the protein-bound probe relative to the free probe. Too low of a probe concentration, however, would lead to increased errors in anisotropy measurements. It is, thus, necessary to select a probe concentration that will provide reliable anisotropy signal. As shown in FIG. 1A, 10 nM of the FITC-16mer Nrf2 peptide gave a reliable anisotropy measurement that is within the fluorescence linear range. Concentrations higher than 10 nM did not significantly improve the coefficient of variation, while at lower concentrations, the anisotropy signals fluctuate as the errors become more prominent due to background noise in the fluorescence measurements.

The equilibration time required for the assay was determined by following the increase in anisotropy signal every 10 min over a 3-h incubation period after mixing the human Keap1 Kelch domain protein with the fluorescent probe. The time it took for the anisotropy signal to plateau was used as the binding period for all of the assays. The equilibration was complete within 30 min at room temperature, which was selected as the incubation time for the FP assay.

Comparison of Fluorophores for the FP Assay

In order to select the best fluorophore for the FP assay, the 9mer Nrf2 peptide amide was also labeled with BODIPY-FL, Cy3B, and Cy5. The BODIPY-FL dye is a known replacement for fluorescein with higher extinction coefficient (>80,000 $M^{-1}cm^{-1}$), high quantum yield (1.0 in water), insensitivity to environment such as pH, and sharp excitation and emission bands. The cyanine dyes, Cy3B and Cy5, are also known for their excellent fluorescence properties and high water solubility, which may improve the solubility of the labeled compound in aqueous assay buffers. The Cy3B dye is a 'brighter' derivative of Cy3 and could be better suited for FP application due to its increased quantum yield and fluorescence lifetime. The ranking of the fluorophores for FP assay application was ascertained by determining the $K_d$ and dynamic range of each probe to the Keap1 Kelch domain under the same assay conditions developed for FITC-labeled Nrf2 peptides. In order to determine the dynamic range for each of the probes, 10 nM of each probe was incubated with Keap1 Kelch domain at varying concentrations for 30 min at room temperature.

Figure 6:
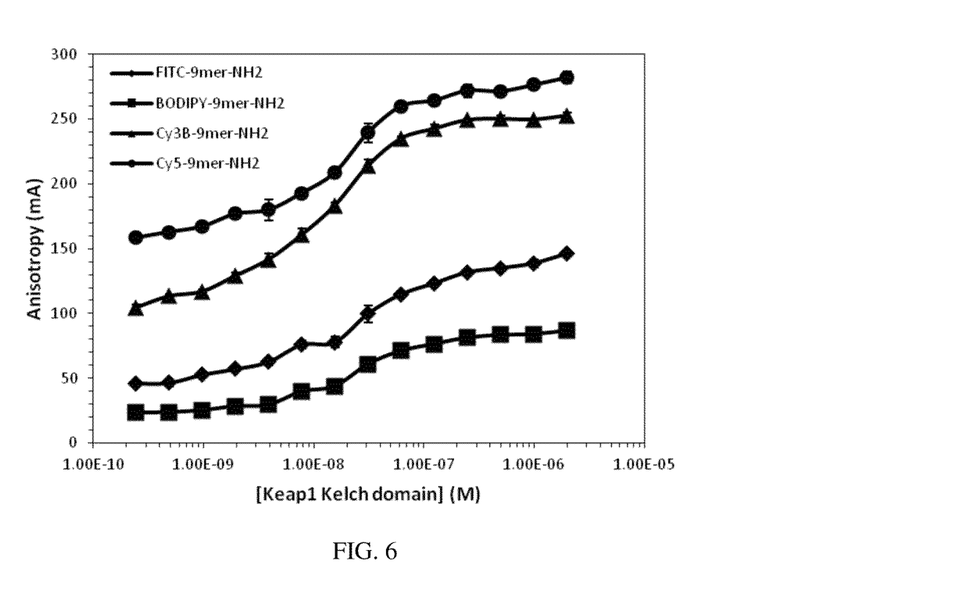
FIG. 6 displays the anisotropy of four 9mer Nrf2 peptide probes plotted as a function of Keap1 Kelch domain concentrations.

As shown in Table 4 and FIG. 6, BODIPY labeled 9mer Nrf2 peptide amide gave the lowest dynamic range of the four fluorescently-labeled peptides with an assay window of 66.5 mA. The FITC-labeled 9mer Nrf2 amide gave the third largest assay window with an anisotropy change of 109.8 mA, while the Cy3B and Cy5-labeled peptide gave assay windows of 167.7 and 143.2 mA, respectively. The cyanine labeled peptides had slightly higher binding affinity to Keap1 Kelch domain, while BODIPY-9mer Nrf2 peptide amide showed similar binding affinity to the FITC-labeled peptide.

In order to compare the performance of fluorophores for the assay. Z'-factor was calculated for each probe. The Z'-factor is a measure of assay performance that incorporates the assay window and the random error present in the FP measurement. According to the Z'-factor model, values greater than 0.5 indicate excellent assays which may be readily adapted to high throughput applications. As shown in Table 4, all of the fluorophores perform well under the assay conditions with the Z'-factors greater than 0.8. Considering the cost of Cy5 and Cy3B label reagents, FITC-labeled peptide is still a viable option for HTS application as evidenced by the relatively high Z'-factor.

TABLE 4

The 9mer Nrf2 peptide amides labeled by different fluorophores and the $K_d$ and dynamic ranges compared under the FP assay conditions developed.[a]

| Fluorophore | Filter set | Δ mA | Z'-factor | $K_d$ (nM) |
|---|---|---|---|---|
| Fluorescein | 485/535 | 109.8 | 0.915 | 25.6 ± 10.8 |
| BODIPY-FL | 485/535 | 66.6 | 0.862 | 20.0 ± 4.18 |
| Cy3B | 530/590 | 167.7 | 0.933 | 6.07 ± 4.4 |
| Cy5 | 620/680 | 143.2 | 0.821 | 11.4 ± 7.2 |

[a]Anisotropy measurements for the FP binding assay were performed as described under methods section.
$K_d$ values were calculated from anisotropy of ligands using equation 5 and ΔmA values were calculated as the difference in the free and the highest observed anisotropy of the respective ligands.
The Z'-factors were calculated as described by Zhang et al[40].

The Effect of DMSO on Anisotropy Measurement

Compounds in chemical libraries used in high throughput screening are often dissolved in DMSO. The effect of DMSO on one embodiment of the presently described FP assay was determined by measuring the anisotropy change of the Keap1-bound and free fluorescent probe in presence of DMSO in the assay solutions at concentrations up to 20%. 20 μL of the assay buffer containing varying concentrations of DMSO and 10 μL of 40 nM FITC-9mer Nrf2 peptide amide was added to a Corning 3575 384-well plate. Then, either 10 μL of 400 nM Keap1 Kelch domain protein or 10 μL of buffer were added to each well and the plate was centrifuged for 2 min at 370×g. The plate was incubated for 30 min in the dark at room temperature prior to the anisotropy measurement.

Figure 7:
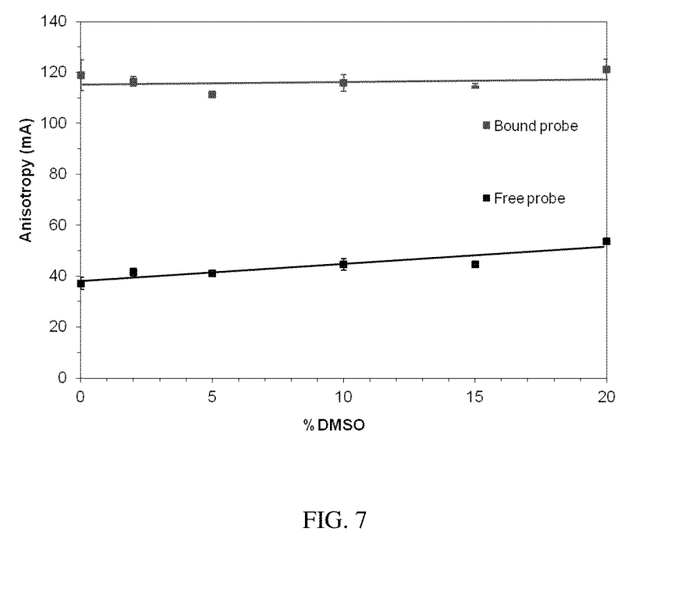
FIG. 7 shows the effect of DMSO concentration on the dynamic range of the assay was evaluated by measuring the anisotropy of the bound and the free probe in the presence of varying concentrations of DMSO.
Figure 8:
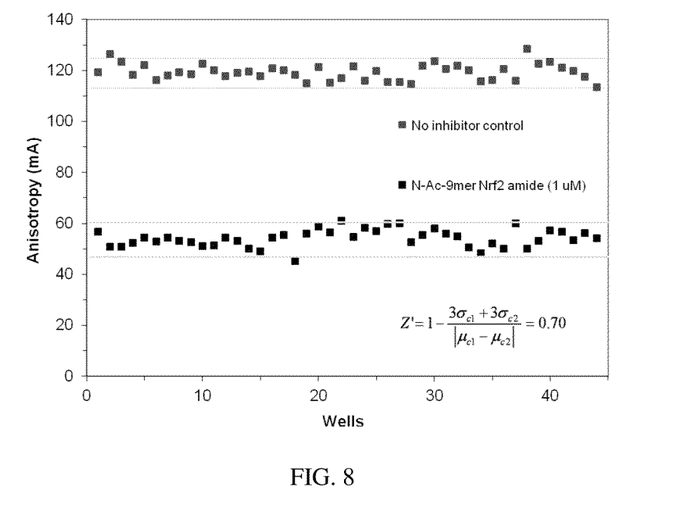
FIG. 8 shows an analysis of the Z'-factor of the FP assay using 10 nM FITC-9mer Nrf2 peptide amide as the probe and 100 nM Keap1 Kelch domain in the presence or absence of 1 µM N-acetyl-9mer Nrf2 peptide amide with 95% tolerance intervals shown.

Generally, the DMSO concentration for HTS assays range from 0.5-5%, and for Fβ-based assays, increasing the viscosity of the solution is not desirable as the polarization of the fluorescent molecules may increase due to slower rotation in viscous solution. As shown in FIG. 7, the increase in concentration of DMSO does not significantly affect the anisotropy of the bound state of the ligand, while the anisotropy of the free ligand slowly increases with increasing concentration of DMSO. This means that the fluorescence polarization of the ligand bound to a macromolecule is less affected by the viscosity of the solution, but the free ligand is more susceptible to changes in viscosity. As shown in FIG. 7, one embodiment of the FP assay of the present invention tolerates fairly high concentrations of DMSO with less than 15% change in the dynamic range of the assay at 10% DMSO concentration. Since the concentration of DMSO in HTS assays usually falls under 5%, the DMSO tolerated by one embodiment of the FP assay of the present invention is still acceptable for high throughput applications.

Surface Plasmon Resonance (SPR) Binding Assay

The binding affinities of FITC-labeled Nrf2 peptides using the FP assay were confirmed by an SPR competition binding assay. This assay was carried out on a Biacore 3000 biosensor (GE Healthcare, Piscataway, N.J.) using the immobilized N-biotinylated 16mer Nrf2 peptide as the ligand and Keap1 Kelch domain as the analyte. The surface of a CM5 chip was first activated using the standard amine coupling method. Equal volumes of 0.1 M NHS and 0.4 M EDC were mixed and injected into flow cell (Fc) 1 and 2 at a flow rate of 10 μL/min for 7 min, followed by the injection of streptavidin (200 μg/mL) for 7 min. Finally, ethanolamine (0.1 M) was injected through the flow cell to deactivate the remaining NHS esters on the chip surface. Around 7000 RU of streptavidin was immobilized on each flow cell. A solution of N-biotinyl 16mer Nrf2 peptide was diluted to 10 nM using 10 mM HEPES buffer, pH 7.4 containing 150 mM NaCl, 3.4 mM EDTA, and 0.005% Tween-20 (HBS running buffer) and injected through Fc2 at a flow rate of 10 μL/min. The streptavidin surface was slowly saturated by the biotin-labeled Nrf2 peptide and the maximum immobilization level of ~300 RU was finally achieved. Fc1 of the chip without the Nrf2 peptide was used as the blank surface.

All interactions between Keap1 Kelch domain and the immobilized biotin-16mer Nrf2 peptide were carried out with a 1-min association time and a 3-min dissociation time at a flow rate of 30 μL/min. The sensor chip surfaces were regenerated with a 0.5-min injection of 1M NaCl at a flow rate of 30 μL/min. The regeneration step was followed by two buffer washes of IFC and the needle. The data analysis was performed using BIAevaluation software v4.1 by measuring the slope of the initial association phase from the SPR sensograms after double subtraction of responses from the reference surface and the zero blank in the absence of Keap1 Kelch domain. To calculate the concentrations of free (i.e., unbound) Keap1 Kelch domain, a standard curve was constructed using serially diluted solutions of Keap1 Kelch domain with concentrations covering the observed Keap1 Kelch domain concentrations in the competition assay. For competition binding assay, a solution of Keap1 Kelch domain at a fixed concentration of 20 nM or 40 nM and various concentrations of inhibitory Nrf2 peptides ranging from 0 nM to 1 μM was introduced over each surface (Fc1 and Fc2). The slopes of initial association phase obtained from sensograms were used to calculate the concentrations of free Keap1 Kelch domain and the fraction of Keap1 Kelch domain (f) bound to the inhibitory peptides. The $f_b$ data obtained was fitted to the quadratic equation (5) to derive $K_d$ using, where $R_t$ is the concentration of Keap1 kelch domain used, which was fixed at 20 nM or 40 nM, and $L_t$ is the concentration of each inhibitory Nrf2 peptide.

Figure 3:
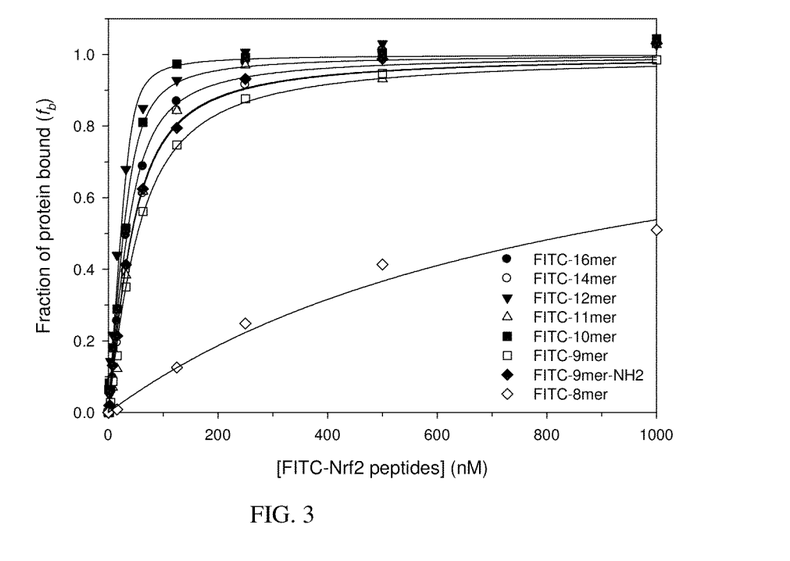
FIG. 3 displays the fractions of Keap1 Kelch domain bound to FITC-labeled Nrf2 peptides against FITC-labeled Nrf2 peptide concentrations.
Figure 4:
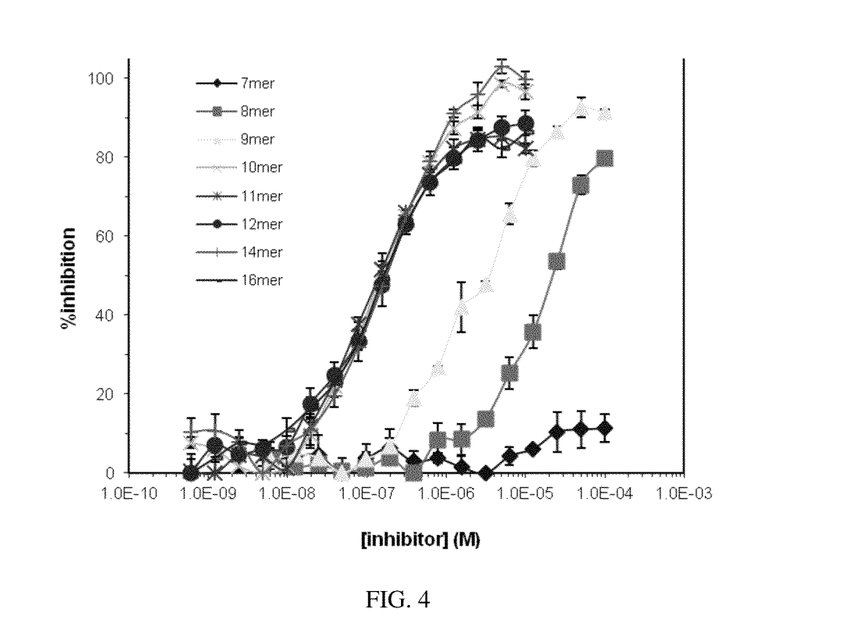
FIG. 4 shows the inhibition of binding of FITC-9mer Nrf2 amide to Keap1 Kelch domain by Nrf2 peptides as determined in the Fβ-based competition assay.

As shown in FIG. 3 and Table 2, the general trend for the binding affinity of the Nrf2 peptides was similar to the results obtained by one embodiment of the presently described FP assay. Although the binding affinity of the 10mer and 12mer Nrf2 peptides were better than expected, the general trend shows that the binding affinity increases with increasing peptide length. The SPR data also indicates that most of the bonding interaction between Keap1 Kelch domain are within FITC-9mer Nrf2 peptide as the binding affinity of 9mer to 16mer Nrf2 peptides are quite similar. Consistent with the FP assay, the 8mer Nrf2 peptide binds much weaker to Keap1 Kelch domain and the binding affinity is more than 20-fold higher than that of the FITC-9mer Nrf2 peptide.

TABLE 2

The binding affinity of FITC-labeled Nrf2 peptides determined by SPR.[a]

| Peptide | | $K_d$ (nM) |
|---|---|---|
| FITC-8mer Nrf2 | FITC-DEETGEFL-OH | ~835 |
| FITC-9mer Nrf2 | FITC-LDEETGEFL-OH | 33.2 ± 4.4 |
| FITC-9mer Nrf2-NH$_2$ | FITC-LDEETGEFL-NH$_2$ | 22.3 ± 4.2 |
| FITC-10mer Nrf2 | FITC-QLDEETGEFL-OH | 11.9 ± 0.3 |
| FITC-11mer Nrf2 | FITC-LQLDEETGEFL-OH | 24.4 ± 9.8 |
| FITC-12mer Nrf2 | FITC-QLQLDEETGEFL-OH | 25.1 ± 0.6 |
| FITC-14mer Nrf2 | FITC-FAQLQLDEETGEFL-OH | 22.8 ± 6.0 |
| FITC-16mer Nrf2 | FITC-AFFAQLQLDEETGEFL-OH | 14.5 ± 4.4 |

[a]The SPR binding assay was performed as described under methods section. The $K_d$ were determined by regression analysis using equation 5.

FP Competition Assays to Determine Inhibitory Potency of Keap1-Nrf2 Interaction

A competition assay using the conditions described above was established and miniaturized to 384-well plate format to determine the potency of inhibitors of Keap1-Nrf2 interaction. A Packard Bioscience (now Perkin Elmer) Multiprobe II HT EXpanded liquid handling robot was used to deliver small volumes of solutions to each of the 384 wells. Each well had a final volume of 40 μL that consisted of 10 μL of 40 nM FITC-9mer Nrf2 peptide amide and 10 μL of 400 nM Keap1 Kelch domain protein, 10 μL of HEPES buffer, and 10 μL of an inhibitor sample of varying concentrations. The binding experiments were performed in triplicates with initial concentration of the inhibitor typically set between 10 μM and 100 μM depending on the inhibitor potency and serially diluted 2-fold to give a concentration range down to 0.5 nM or 5 nM. The plate was centrifuged at 370×g for 2 min to get rid of any air bubbles in the assay solution and to ensure thorough mixing. The plate was covered and allowed to equilibrate for 30 min at room temperature. The plate was centrifuged again prior to fluorescence polarization measurements.

The % inhibition of the competitor at each concentration point were determined by using equation (6) and the IC$_{50}$ of an inhibitor was determined from the plot of % inhibition against inhibitor concentration using equation (7).

$$\% \text{ inhibition} = \frac{A_{top} - A_{obs}}{A_{top} - A_{bottom}} \times 100\% \quad (6)$$

$$A = A_{bottom} + \frac{A_{top} + A_{bottom}}{1 + 10^{n(x - \log IC_{50})}} \quad (7)$$

IC$_{50}$ is the concentration of an inhibitor needed to inhibit 50% binding of the fluorescently labeled peptide probe, x is the log of the inhibitor concentration, and n is the Hill slope that describes the steepness of the curve. The values of $A_{top}$, $A_{bottom}$, and $A_{obs}$ in the equations refer to the anisotropy of the wells containing Keap1 and the probe, the anisotropy of the free probe, and the observed anisotropy for the wells containing the inhibitors at a range of concentrations under the assay conditions. The IC$_{50}$ values determined were used to derive $K_i$ of the inhibitors using equation (8).

$$IC_{50} = \left( \frac{f_b - K_d}{(1 - f_b)(2 - f_b)} + \frac{f_b \times L_0}{2} \right) \left( \frac{K_i(2 - f_b)}{K_d \times f_b} + 1 \right) \quad (8)$$

Pilot Screen of NCI Diversity Set II and Clinical Collection

For the measurement of Z'-factor, a 384-well plate was prepared with 10 nM FITC-9mer Nrf2 amide and 100 nM Keap1 Kelch domain in 10 mM HEPES buffer in the presence or absence of 1 μMl of N-acetyl 9mer Nrf2 amide (44 replicates each). From the anisotropy of 10 nM FITC-9mer Nrf2 peptide amide in the presence of 100 nM Keap1 Kelch domain (~75% bound—as the negative control) and the anisotropy of 10 nM FITC-9mer Nrf2 peptide amide in the presence of 100 nM Keap1 Kelch domain and 1 μM N-acetyl-9mer-Nrf2 peptide amide (~80% inhibition—as the positive control), Z'-factor was calculated by the equation $$Z' = 1 - \frac{3\sigma_{c1} + 3\sigma_{c2}}{|\mu_{c1} - \mu_{c2}|} \quad \text{Eq. (9)}$$

where $\mu_{c1}$, and $\mu_{c2}$ are the mean values of the positive control and negative control wells, respectively, and $\sigma_{c1}$ and $\sigma_{c2}$ are the standard deviation of the positive and negative control wells, respectively. When comparing the different fluorescent probes, only the top and bottom replicates were used to derive Z'-factor.

Using the FP Assay

The preferred FITC-9mer Nrf2 peptide amide as the probe was used to differentiate a series of Nrf2 peptide as inhibitors of Keap1-Nrf2 interaction using the above described competition binding assay. The concentration of Keap1 Kelch domain was fixed at 100 nM to give $f_b$ between 0.7 and 0.8 at a fixed FITC-9mer Nrf2 peptide amide probe concentration within 2 $K_d$ of its affinity at 10 nM to satisfy nonstoichiometric titration conditions and achieve sufficient anisotropy level. The results from the competition assay are summarized in Table 3 and FIG. 5. The binding affinities of the Nrf2 peptides against Keap1 Kelch domain determined by the FP competition assay were similar to the trend in binding affinities for the series of Nrf2 peptides obtained by the SPR method. The inhibitory activity of the Nrf2 peptide increases with increasing peptide length as evidenced by the higher $IC_{50}$ values for the shorter 8mer and 9mer Nrf2 peptides ($IC_{50}$=30.5 and 3.48 µM, respectively) and lower $IC_{50}$ values for the longer 10mer to the 16mer Nrf2 peptides.

Figure 5:
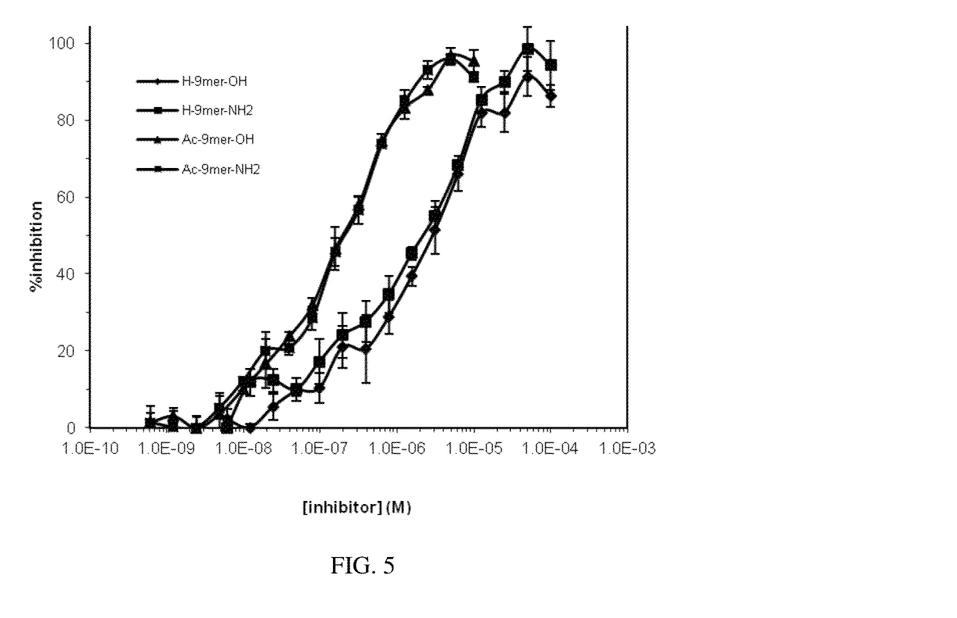
FIG. 5 shows the inhibition of Keap1 Kelch domain-Nrf2 interaction by a series of 9mer Nrf2 peptides.

The FP data of this competition binding assay also indicates that the binding affinity of the 16mer Nrf2 peptide is stronger than the shorter Nrf2 and is in good agreement with previously reported values. The binding of the 16mer Nrf2 peptide (AFFAQLQLDEETGEFL) (SEQ ID NO:7) was the strongest in the assay with an $IC_{50}$ of 163 nM and a calculated $K_i$ of 37.4 nM. The resolution of inhibitor potencies by a FP assay under nonstoichiometric conditions may be limited by the $K_d$ of the probe used. When the inhibitor potency is much stronger relative to the probe ($K_i \ll K_d$), the $K_d$ in equation (8) is in linear relationship with the $IC_{50}$ value. Thus, $IC_{50}$ of potent inhibitors will be independent of inhibitor potency and become directly proportional to the $K_d$ of the probe used. However, the trend in binding affinity of Nrf2 peptide inhibitors determined by the FP assay was in good agreement with the results previously obtained by the SPR assay, which indicates that the resolution of binding affinities between the Nrf2 peptides is not limited by the FP competition assay conditions. The presently claimed assay is able to clearly differentiate the binding affinity of Nrf2 peptides of varying length.

The inhibitory activity of the N- and or C-terminal capped 9mer Nrf2 peptides were determined by the FP competition assay. As shown in FIG. 5, a significant 14× increase was observed as a result of N-terminal acetylation of 9mer Nrf2 peptide ($IC_{50}$=194 µM). A similar increase of 18× was observed for the N-acetylation of 9mer Nrf2 peptide amide ($IC_{50}$=196 nM). While the effect of neutralizing the positive charge at the N-terminus of 9mer Nrf2 peptides by acetylation was obvious, the C-terminal capping as an amide had no effect on the binding affinity. The N-terminal labeling of the Nrf2 peptides by the fluorescent reagents like FITC similarly increased the binding affinity of the shorter Nrf2 peptides as N-acetylation.

TABLE 3

The inhibition of Keap1 Kelch domain-Nrf2 interaction determined for the different Nrf2-peptides using the FP-based competition assay developed.[a]

| Peptide | | $IC_{50}$ (µM) | $K_i$ (nM)[c] |
|---|---|---|---|
| 7mer Nrf2 | H-EETGEFL-OH | >>100 | —[d] |
| 8mer Nrf2 | H-DEETGEFL-OH | 21.7 ± 20.1[b] | 7010 |
| 8mer Nrf2-NH₂ | H-DEETGEFL-NH₂ | 30.5 ± 22.7[b] | 9870 |
| 9mer Nrf2 | H-LDEETGEFL-OH | 3.48 ± 0.919 | 865 |
| 9mer Nrf2-NH₂ | H-LDEETGEFL-NH₂ | 3.57 ± 2.2 | 1140 |
| Ac-9mer Nrf2 | Ac-LDEETGEFL-OH | 0.194 ± 0.049 | 47.4 |
| Ac-9mer Nrf2-NH₂ | Ac-LDEETGEFL-NH₂ | 0.196 ± 0.032 | 48.1 |
| 10mer Nrf2 | H-QLDEETGEFL-OH | 0.272 ± 0.026 | 72.7 |
| 11mer Nrf2 | H-LQLDEETGEFL-OH | 0.298 ± 0.033 | 81.1 |
| 12mer Nrf2 | H-QLQLDEETGEFL-OH | 0.249 ± 0.022 | 65.2 |
| 14mer Nrf2 | H-FAQLQLDEETGEFL-OH | 0.243 ± 0.020 | 63.3 |
| 16mer Nrf2 | H-AFFAQLQLDEETGEFL-OH | 0.163 ± 0.011 | 37.4 |

[a]The fluorescence polarization measurements for the competition assay were performed as described in the methods section. The reported $IC_{50}$ values were determined by regression analysis using equation 6.
[b]$IC_{50}$ was estimated using the anisotropy value of the 9mer Nrf2 at 100% inhibition
[c]$K_i$ was derived using equation (8) with 100 nM Keap1 Kelch domain at a fixed L0 = 10 nM to give fb = 0.75.[30]
[d]$K_i$ was not calculated due to low binding affinity.

In summary, the competition binding assay using FITC-9mer Nrf2 amide as the probe was used to rank the binding affinities of 7mer to 16mer Nrf2 peptide inhibitors. The binding affinity of the 16mer Nrf2 peptide (H-AFFAQLQLDEETGEFL-OH, $K_i$=37.4 nM) (SEQ ID NO:7) was consistent with the reported value and is the strongest in affinity to Keap1 in our Fβ-based competition assay. The FP assay results show that the binding affinities of 7mer and 8mer Nrf2 peptides are significantly lower than the longer peptides, indicating a overall trend that the binding affinity increases as increasing peptide length. The FP assay of the N-acetylated 9mer Nrf2 peptides showed similar binding affinities to the longer peptides with Keap1. We have successfully used our FP assay developed here in the screening of the NCI Diversity Set II of 1364 compounds and the NIH Clinical Collection (NCC) of 446 compounds and the FP assay has also been adapted to 1534-well format and successfully used by the Broad Institute in the screening of MLPCN library of 330,000 compounds for the discovery of small molecule inhibitors of Keap1-Nrf2 interaction. Nrf2 is the principle mediator of ARE expression, thus the disruption of Keap1:Nrf2 complex is believed to be an effective strategy in inducing the expression of antioxidant and cytoprotective genes.

We claim:

1. A method for identifying an agent that inhibits a Keap1-Nrf2 interaction, the method comprising:
   (a) providing a mixture comprising a Keap1-Kelch domain protein and a fluorescently labeled Nrf2 peptide that is capable of binding the Keap1-Kelch domain protein;
   (b) adding a test agent to the mixture;
   (c) determining the difference in the amount of fluorescently labeled Nrf2 peptide bound to the Keap1-Kelch domain protein in the presence and absence of the test agent; and
   (d) identifying the test agent as an inhibitor of the Keap1-Nrf2 interaction if the amount of fluorescently labeled Nrf2 peptide bound to the Keap1-Kelch domain protein in the presence of the test agent is less than in the absence of the test agent; wherein the fluorescently labeled Nrf2 peptide has the sequence Leu-Asp-Glu-Glu-Thr-Gly-Glu-Phe-Leu-NH$_2$ (SEQ ID NO:12).

2. The method of claim 1, wherein step (c) comprises:
   (c1) determining the fluorescence polarization value;
   (c2) determining the fraction of fluorescently labeled Nrf2 peptide bound to the Keap1-Kelch domain protein from the fluorescence polarization value; and
   (c3) comparing the fraction of fluorescently labeled Nrf2 peptide bound to the Keap1-Kelch domain protein to the fraction of fluorescently labeled Nrf2 peptide bound to the Keap1-Kelch domain protein in the absence of the test compound.

3. The method of claim 2, wherein step (c2) comprises converting the fluorescence polarization values to anisotropy values.

4. The method of claim 3 comprising calculating the Z'-factor from the anisotropy values.

5. The method of claim 4, wherein a test agent is identified as an inhibitor if the Z'-factor is greater than 3.

6. The method of claim 1 further comprising performing the steps (a)-(c) a plurality of times, each time with a different concentration of the agent.

7. The method of claim 6 further comprising determining a K$_i$ value for the agent.

8. The method of claim 1, wherein the fluorescently labeled Nrf2 peptide is labeled by a fluorophore selected from the group consisting of fluorescein isothiocyanate, BODIPY-FL, Cy3B and Cy5.

* * * * *

SEQUENCE LISTING

<160> NUMBER OF SEQ ID NOS: 15

<210> SEQ ID NO 1
<211> LENGTH: 8
<212> TYPE: PRT
<213> ORGANISM: Homo sapiens

<400> SEQUENCE: 1

Asp Glu Glu Thr Gly Glu Phe Leu
1               5

<210> SEQ ID NO 2
<211> LENGTH: 9
<212> TYPE: PRT
<213> ORGANISM: Homo sapiens

<400> SEQUENCE: 2

Leu Asp Glu Glu Thr Gly Glu Phe Leu
1               5

<210> SEQ ID NO 3
<211> LENGTH: 10
<212> TYPE: PRT
<213> ORGANISM: Homo sapiens

<400> SEQUENCE: 3

Gln Leu Asp Glu Glu Thr Gly Glu Phe Leu
1               5                   10

<210> SEQ ID NO 4
<211> LENGTH: 11
<212> TYPE: PRT
<213> ORGANISM: Homo sapiens

<400> SEQUENCE: 4

Leu Gln Leu Asp Glu Glu Thr Gly Glu Phe Leu
1               5                   10

<210> SEQ ID NO 5
<211> LENGTH: 12
<212> TYPE: PRT
<213> ORGANISM: Homo sapiens

<400> SEQUENCE: 5

Gln Leu Gln Leu Asp Glu Glu Thr Gly Glu Phe Leu
1               5                   10

<210> SEQ ID NO 6
<211> LENGTH: 14
<212> TYPE: PRT
<213> ORGANISM: Homo sapiens

<400> SEQUENCE: 6

Phe Ala Gln Leu Gln Leu Asp Glu Glu Thr Gly Glu Phe Leu
1               5                   10

<210> SEQ ID NO 7
<211> LENGTH: 16
<212> TYPE: PRT
<213> ORGANISM: Homo sapiens

<400> SEQUENCE: 7

Ala Phe Phe Ala Gln Leu Gln Leu Asp Glu Glu Thr Gly Glu Phe Leu
1               5                   10                  15

<210> SEQ ID NO 8
<211> LENGTH: 4
<212> TYPE: PRT
<213> ORGANISM: Homo sapiens

<400> SEQUENCE: 8

Glu Thr Gly Glu
1

<210> SEQ ID NO 9
<211> LENGTH: 7
<212> TYPE: PRT
<213> ORGANISM: Homo sapiens

<400> SEQUENCE: 9

Glu Glu Thr Gly Glu Phe Leu
1               5

<210> SEQ ID NO 10
<211> LENGTH: 14
<212> TYPE: PRT
<213> ORGANISM: Homo sapiens

<400> SEQUENCE: 10

Leu Gln Leu Asp Glu Glu Thr Gly Glu Phe Leu Pro Ile Gln
1               5                   10

<210> SEQ ID NO 11
<211> LENGTH: 10
<212> TYPE: PRT
<213> ORGANISM: Homo sapiens

<400> SEQUENCE: 11

Leu Asp Glu Glu Thr Gly Glu Phe Leu Pro
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic peptide probe
<220> FEATURE:
<221> NAME/KEY: AMIDATION
<222> LOCATION: (9)..(9)

<400> SEQUENCE: 12

Leu Asp Glu Glu Thr Gly Glu Phe Leu
1               5

<210> SEQ ID NO 13
<211> LENGTH: 9
<212> TYPE: PRT
<213> ORGANISM: Artificial
<220> FEATURE:
<223> OTHER INFORMATION: Synthetic peptide probe
<220> FEATURE:
<221> NAME/KEY: ACETYLATION
<222> LOCATION: (1)..(1)
<223> OTHER INFORMATION: N-terminal

<400> SEQUENCE: 13

Leu Asp Glu Glu Thr Gly Glu Phe Leu
1               5

<210> SEQ ID NO 14

```
<211> LENGTH: 8
<212> TYPE: PRT
<213> ORGANISM: Artificial
<220> FEATURE:
<223> OTHER INFORMATION: Synthetic peptide probe
<220> FEATURE:
<221> NAME/KEY: AMIDATION
<222> LOCATION: (8)..(8)

<400> SEQUENCE: 14

Asp Glu Glu Thr Gly Glu Phe Leu
1               5

<210> SEQ ID NO 15
<211> LENGTH: 308
<212> TYPE: PRT
<213> ORGANISM: Homo sapiens

<400> SEQUENCE: 15

Gly Ser Ser His His His His His Ser Ser Gly Leu Val Pro Arg
1               5                   10                  15

Gly Ser His Ala Pro Lys Val Gly Arg Leu Ile Tyr Thr Ala Gly
                20                  25                  30

Tyr Phe Arg Gln Ser Leu Ser Tyr Leu Glu Ala Tyr Asn Pro Ser Asp
            35                  40                  45

Gly Thr Trp Leu Arg Leu Ala Asp Leu Gln Val Pro Arg Ser Gly Leu
        50                  55                  60

Ala Gly Cys Val Val Gly Gly Leu Leu Tyr Ala Val Gly Gly Arg Asn
65                  70                  75                  80

Asn Ser Pro Asp Gly Asn Thr Asp Ser Ser Ala Leu Asp Cys Tyr Asn
                85                  90                  95

Pro Met Thr Asn Gln Trp Ser Pro Cys Ala Pro Met Ser Val Pro Arg
            100                 105                 110

Asn Arg Ile Gly Val Gly Val Ile Asp Gly His Ile Tyr Ala Val Gly
        115                 120                 125

Gly Ser His Gly Cys Ile His His Asn Ser Val Glu Arg Tyr Glu Pro
    130                 135                 140

Glu Arg Asp Glu Trp His Leu Val Ala Pro Met Leu Thr Arg Arg Ile
145                 150                 155                 160

Gly Val Gly Val Ala Val Leu Asn Arg Leu Leu Tyr Ala Val Gly Gly
                165                 170                 175

Phe Asp Gly Thr Asn Arg Leu Asn Ser Ala Glu Cys Tyr Tyr Pro Glu
            180                 185                 190

Arg Asn Glu Trp Arg Met Ile Thr Ala Met Asn Thr Ile Arg Ser Gly
        195                 200                 205

Ala Gly Val Cys Val Leu His Asn Cys Ile Tyr Ala Ala Gly Gly Tyr
    210                 215                 220

Asp Gly Gln Asp Gln Leu Asn Ser Val Glu Arg Tyr Asp Val Glu Thr
225                 230                 235                 240

Glu Thr Trp Thr Phe Val Ala Pro Met Lys His Arg Arg Ser Ala Leu
                245                 250                 255

Gly Ile Thr Val His Gln Gly Arg Ile Tyr Val Leu Gly Gly Tyr Asp
            260                 265                 270

Gly His Thr Phe Leu Asp Ser Val Glu Cys Tyr Asp Pro Asp Thr Asp
        275                 280                 285

Thr Trp Ser Glu Val Thr Arg Met Thr Ser Gly Arg Ser Gly Val Gly
    290                 295                 300
```

Val Ala Val Thr
305